United States Patent
Miltner et al.

(10) Patent No.: US 6,707,554 B1
(45) Date of Patent: Mar. 16, 2004

(54) METHOD FOR THE PHOTOMETRIC ANALYSIS OF TEST ELEMENTS

(75) Inventors: Karl Miltner, Frankenthal (DE); Uwe Ruppender, Mannheim (DE); Christian Wersig, Birkenheide (DE); Volker Zimmer, Dossenheim (DE)

(73) Assignee: Roche Diagnostics GmbH, Mannheim (DE)

( * ) Notice: Subject to any disclaimer, the term of this patent is extended or adjusted under 35 U.S.C. 154(b) by 0 days.

(21) Appl. No.: 09/806,115

(22) PCT Filed: Sep. 29, 1999

(86) PCT No.: PCT/EP99/07222

§ 371 (c)(1),
(2), (4) Date: Sep. 4, 2001

(87) PCT Pub. No.: WO00/19185

PCT Pub. Date: Apr. 6, 2000

(30) Foreign Application Priority Data

Sep. 29, 1998 (DE) .......................... 198 44 500

(51) Int. Cl.$^7$ .......................... G01N 21/00; G01N 33/48
(52) U.S. Cl. ...................... 356/433; 356/435; 356/436; 356/39
(58) Field of Search ................ 356/445, 446, 356/39–42, 432, 433, 441, 434–436, 448, 36, 37, 427

(56) References Cited

U.S. PATENT DOCUMENTS

| | | | | |
|---|---|---|---|---|
| 4,755,058 A | * | 7/1988 | Shaffer | 356/408 |
| 4,806,002 A | | 2/1989 | Simeth et al. | 356/445 |
| 5,114,350 A | | 5/1992 | Hewett | 435/288 |
| 5,397,538 A | | 3/1995 | Stark et al. | 422/57 |
| 5,889,585 A | * | 3/1999 | Markart | 356/39 |
| 5,995,236 A | * | 11/1999 | Roth et al. | 356/445 |
| 6,036,919 A | * | 3/2000 | Thym et al. | 422/58 |
| 6,055,060 A | * | 4/2000 | Bolduan et al. | 356/433 |
| 6,103,197 A | * | 8/2000 | Werner | 422/82.09 |
| 6,574,425 B1 | * | 6/2003 | Weiss et al. | 386/402 |

FOREIGN PATENT DOCUMENTS

| | | | | |
|---|---|---|---|---|
| DE | 19630160 A1 | 1/1998 | | G01N/33/52 |
| EP | 0165535A2 B1 | 12/1985 | | G01N/21/47 |
| EP | 0264562 B1 | 4/1988 | | B41F/33/00 |

* cited by examiner

Primary Examiner—Russell Adams
Assistant Examiner—Andrew Sever
(74) Attorney, Agent, or Firm—Brinks Hofer Gilson & Lione

(57) ABSTRACT

The invention concerns a method for the photometric analysis of test elements with a detection zone which is stable towards positioning tolerances of the detection zone comprising the following steps: activating the first light source to irradiate a first region of the detection zone and detecting the light reflected from the detection zone or transmitted through the detection zone in order to generate a first detection signal (50), activating the second light source to irradiate a second region of the detection zone which is displaced relative to the first region in the direction of the positioning tolerance and detecting the light reflected from the detection zone or transmitted through the detection zone in order to generate a second detection signal (60), comparing the first and the second detection signal and determining whether the first and/or the second detection signal has been obtained by illuminating an area situated completely on the detection zone. The invention also concerns a device to carry out this method and a method for the photometric analysis of a test element with detection of sample application.

29 Claims, 8 Drawing Sheets

Fig. 1
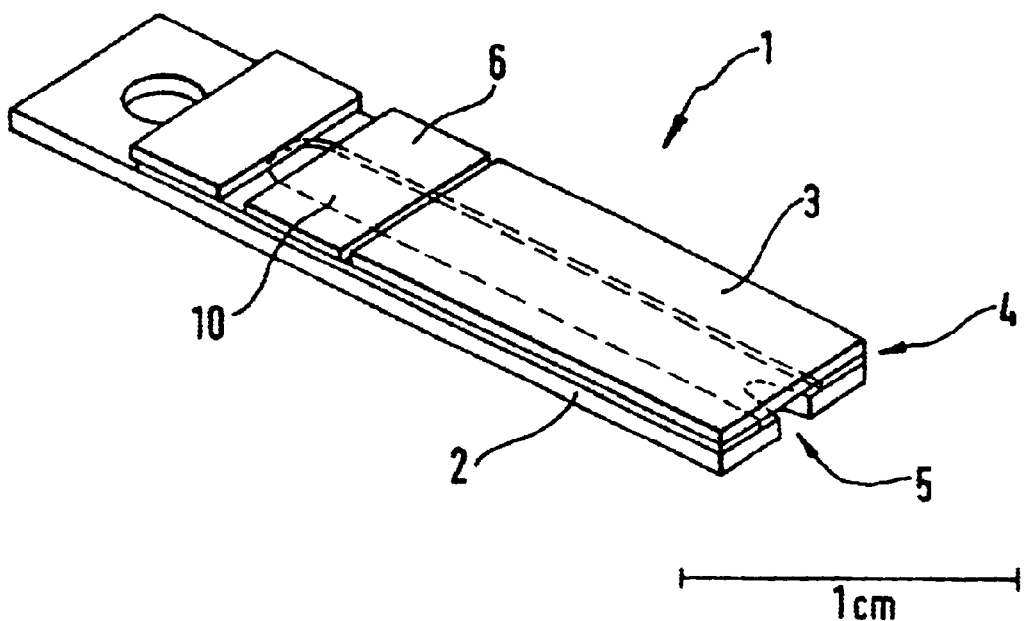
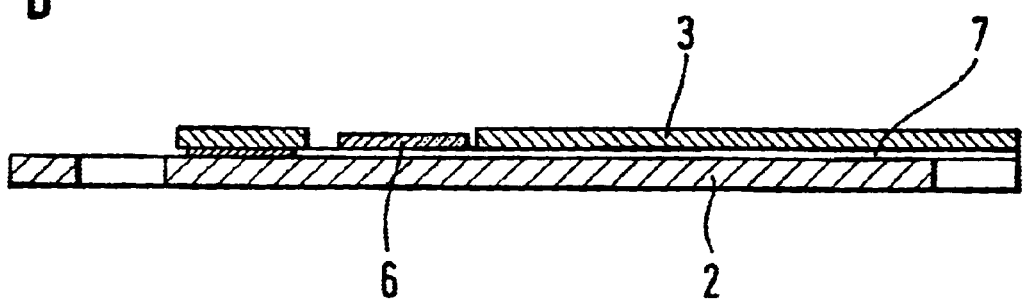

Fig. 5
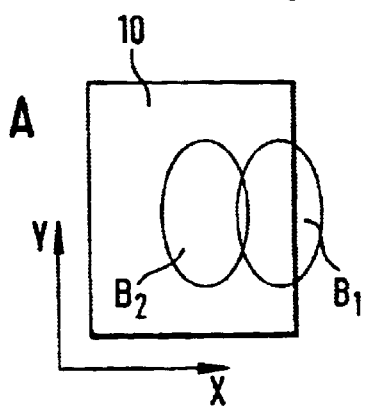
A
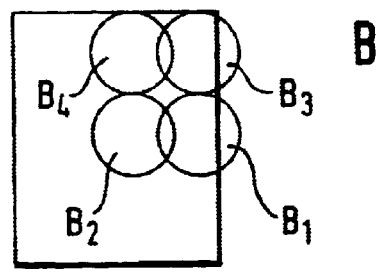
B
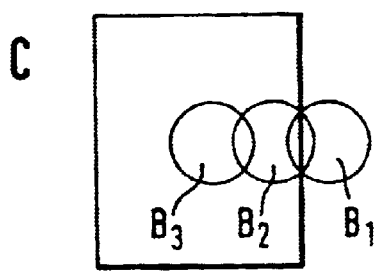
C
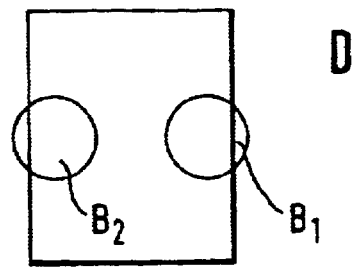
D
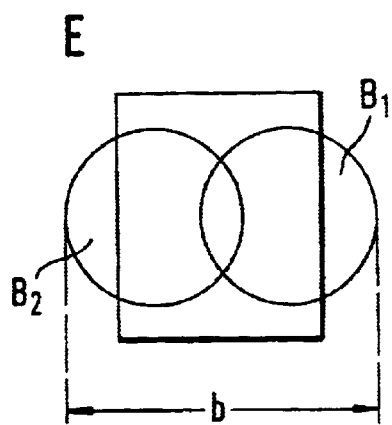
E
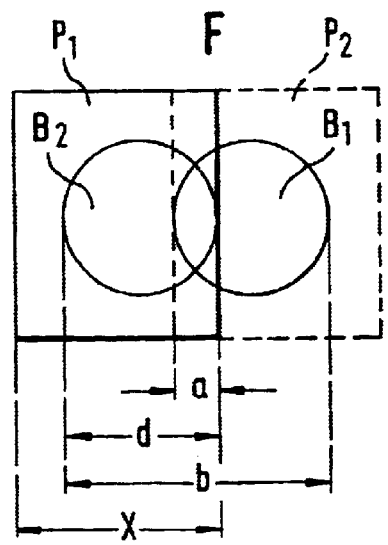
F

METHOD FOR THE PHOTOMETRIC ANALYSIS OF TEST ELEMENTS

BACKGROUND OF THE INVENTION

The invention concerns a method for the photometric analysis of test elements with detection zones, said method being stable in relation to positioning tolerances of the detection zone.

The photometric analysis of test elements is one of the most common methods for rapidly determining the concentration of analytes in samples. Photometric analyses are generally carried out in the field of analytics, environmental analytics and above all in the field of medical diagnostics. Test elements that are analysed photometrically play an important role especially in the field of blood glucose diagnostics from capillary blood.

The general trend in performing analytical tests is to reduce the amounts of sample. This is often due to the fact that only small amounts of sample are present. For example in the field of blood sugar determination, the diabetic himself removes a drop of blood from the finger pad and a reduction in the amount of blood required for the test considerably increases the convenience. This is primarily due to the fact that it is possible to select a smaller depth of cut for the blood collection. A reduction in the amounts of sample is linked to a miniaturization of the test elements and in particular of the detection zones in which the actual reaction of the sample with the analyte takes place. Hence in order to carry out an exact photometric analysis it is necessary to precisely position the detection zone. Numerous test element holders are known in the prior art which allow a quite accurate relative positioning of the detection zone and measurement optics. The European Patent EP-B-0 618 443 (corresponding to U.S. Pat. No. 5,424,035) is mentioned here as an example in which the detection zones of the test element are positioned laterally as well as vertically relative to the measurement optics. The document EP-A-0 319 922 is also mentioned as representative of many other analytical systems which carry out a positioning of test strips. However, the systems known in the prior art operate with detection zones which exceed 5 mm×5 mm. Consequently a positioning in the manner known in the prior art is relatively unproblematic. However, if the lateral dimensions of the detection zone are reduced, great efforts have to be made in the manufacture of the test elements as well as in the positioning within an analytical system in order to obtain reliable analytical results. The object of the present invention was to propose a method and a device of the photometric analysis of test elements which also allow the reliable analysis of test elements with small detection zones.

SUMMARY OF THE INVENTION

This object is achieved by a method for the photometric analysis of test elements in which the test element is placed in a holder in which its detection zone is positioned such that it is disposed relative to an illumination unit with at least two light sources. After the detection zone has been contacted with the sample to be analysed, a first light source is activated in order to irradiate the detection zone. Light reflected from the detection zone or transmitted through the detection zone is detected as a first detection signal. Afterwards a second light source is activated which irradiates a second area of the detection zone which is offset from the first area in the direction of the expected positioning tolerance. The light reflected from this area of transmitted through this area is detected as the second detection signal. The detection signals obtained from the two areas are compared and examined to determine which of the signals was obtained by illumination of an area situated completely in the detection zone. A corresponding detection signal is selected and analysed to determine the analyte concentration in a basically known manner.

A further subject matter of the present invention is a method which can rapidly detect whether an adequate amount of sample liquid has been added to the test element or the detection zone and reports this back to the operator.

In the field of analysis with test elements it is a considerable gain in convenience when the time required to apply sample liquid to a test element can be reduced and when there is also a feedback about whether the applied amount of sample is sufficient. In the case of test elements which utilize an electrochemical principle, it has been common practice for some time to indicate to the user when sample liquid has penetrated into the analytical zone so that he can stop adding sample. In the case of test elements based on electrochemistry this detection can be achieved in a simple manner by a conductivity measurement. However, in the field of optical measurement of test elements such a rapid application detection cannot easily be accomplished. Methods are for example described in the documents U.S. Pat. No. 4,109,261 and EP-A-0 256 806 in which a sample application is detected by the optical system which carries out the measurement and is used as a start signal for awaiting an incubation period. However, in these described methods the user receives no feedback about whether he has applied sufficient sample liquid and can stop further addition. Furthermore optical systems are used in the described methods which detect colour formation in the detection zone of the test element. As shown in FIG. 7 of this application, several seconds pass between contacting the detection zone with sample liquid and the start of colour formation. If for example in the case of a blood sugar test the user has to hold his finger on the test element until a colour reaction is initiated this would be felt by him to be a constraint on his personal freedom. There is therefore a need to reduce the time for the addition or until the detection of the sample liquid. A blood sugar measuring instrument is described for example in EP-A-0 166 876 in which sample application is detected but it does not allow a check of whether the sample quantity is adequate.

Hence a method is proposed as part of the present invention which allows a rapid detection of sample application on a test element. The method according to the invention for the photometric analysis of test elements comprises the following steps:

irradiation of a control area of the detection zone, transporting sample liquid to the detection zone in such a manner that a first zone of the detection zone comes in contact with the sample liquid earlier than a second zone which is at a lateral distance from the first zone monitoring the radiation reflected from the control area or transmitted through the control area, detecting presence of sample liquid in the control area as a result of a change of the reflected or transmitted radiation irradiating a detection area of the detection zone detecting irradiation which has been reflected from the detection area or transmitted through the detection area analysing the detected radiation in order to determine the concentration of an analyte in the sample liquid, characterized in that
when the presence of sample liquid is detected in the control area, a signal is emitted so that the supply of sample liquid can be terminated.

In the following the method according to the invention for compensating positioning tolerances is described first.

A device with which the method according to the invention can be carried out has a holder in which a test element is positioned relative to an illumination unit which is also part of the device. Holders that are known in the prior art and especially the holder described in EP-B-0 618 443 can be used in the following invention. Despite the inventive procedure which stabilizes the analysis in relation to positioning tolerances, it is desirable that the holder already results in a positioning of the detection zone that is as accurate as possible. However, the positioning tolerances cannot be reduced below a certain threshold which becomes clearer when one considers the individual factors that impact on the positioning tolerances. The analytical system already results in a number of tolerances for a relative positioning of the holder and illumination unit. Further tolerances are caused by the positioning of the test element within the holder since a certain clearance between the test element and holder is necessary so that the user can insert the test element in the holder. Furthermore the test element itself is subject to certain manufacturing tolerances which relate in particular to the width of the test element. Finally tolerances also occur with respect to the position of the detection zone relative to the test element and the carrier material of the test element. Especially in capillary gap test elements the detection zone may be considerably displaced in the direction of the width of the test element which is described below in more detail.

The device according to the invention for photometric analysis additionally comprises an illumination unit with at least a first and a second light source. These light sources are used to illuminate adjacent areas of the detection zone. The light sources are arranged such that the centres of the illuminated areas on the detection zone are displaced relative to one another in the direction of an expected positioning tolerance. This can for example be achieved in that the light sources themselves are displaced relative to one another and radiate essentially perpendicularly onto the detection zone. However, the light sources can also be arranged such that they obliquely irradiate the detection zone and the distance between the irradiated areas is essentially achieved by the slant of the light sources relative to the perpendicular relative to the detection zone. In principle the light sources known in the prior art for diagnostic detection systems are suitable as light sources. Light-emitting diodes are preferred as these have a relatively low energy consumption and yield a relatively narrow band spectrum. Miniaturized light-emitting diodes which can be mounted on a semiconductor circuit board are particularly preferred. Such light-emitting diodes are obtainable in sizes which result in light spots of a suitable size on the detection zone without interposing an optical system. However, in the framework of the present invention it is preferable to use an optical system comprising lenses and optionally apertures in addition to the light sources. It is advantageous to adapt the shape of the irradiated areas to the shape of the detection zone and to the expected tolerances. In the case of a rectangular detection zone it is for example advantageous to illuminate oval areas or even rectangular areas. This can for example be achieved by suitable lenses or apertures.

The present invention also envisages using more than two light sources. If a particularly large positioning tolerance is expected in one direction of the detection zone, it is possible for example to use three light sources which illuminate areas on the detection zone which are displaced in the direction of the expected positioning tolerance. The present invention is also suitable for reducing the impact of positioning tolerances in more than one direction. For example four light sources can be used which illuminate four areas that are arranged in the shape of a square or rectangle. Such an arrangement can prevent measurement errors due to positioning inaccuracies in the direction of the one side of the square as well as in the perpendicular direction.

In a method for photometric analysis of test elements a sample is contacted with the detection zone of the test element. The contacting is understood either as a direct application of the samples on the detection zone or a transport of the sample into the detection zone. The latter is in particular the case for capillary gap test elements in which the sample (usually capillary blood from the finger pad) is guided to the capillary gap and is transported through this into the detection zone. Embodiments are also conceivable in which a solid sample is applied to a fleece by for example rubbing a fleece on an object and the sample is subsequently transported by means of an auxiliary fluid from the fleece to the detection zone as is for example the case in some rapid drug tests. In addition there are chromatographic test strips in which the sample is transported into the detection zone by means of absorbent materials. Hence the aforementioned shows that samples within the sense of the invention are primarily sample liquids such as blood but solid sample materials can also be used.

Sample that has been brought into contact with the detection zone leads to a detectable change of the detection zone in test elements. The generation of detectable changes as a result of a reaction of an analyte contained in the sample with a reagent system is well-known in the prior art and thus does not have to be further elucidated here. However, it is relevant for the present invention that the detectable change can be adequately detected with the light sources and detector that are used. This is the case when a colour is formed in the detection zone which absorbs the radiation emitted by the light sources and thus attenuates the transmitted or reflected light. However, the converse case is also possible in which a dye whose presence is detected photometrically is destroyed by the reaction of the reagent system with an analyte and the actual measured signal is a decrease in the attenuation of the transmitted or reflected light. The term light or light source should be understood in the scope of the invention to encompass wavelength ranges that can be used by optical arrangements i.e. UV and IR in addition to the visual range.

The well-known detectors in the prior art and especially semiconductor detectors can be used for the present invention. It is important to select the detector or detectors such that the radiation reflected from the detection zone or transmitted through the detection zone leads to a signal when the detector is illuminated with this radiation. Detectors which have their sensitivity maximum in the range of the reflected or transmitted radiation can be used advantageously. Optionally it is also possible to use filters which allow the measurement radiation to pass selectively in order to make the detection more stable towards the effects of interfering light.

In order to carry out the method according to the invention a first light source of the illumination unit is firstly activated to irradiate a first area of the detection zone and the signal present at the detector during the activation is recorded as a first detection signal. Subsequently the first light source is deactivated and the second light source is activated to irradiate a second area and the signal present at the detector is recorded as the second detection signal. Electric circuits and methods for activating light sources, especially light-emitting diodes are sufficiently well-known in the prior art. Reference is made by way of example to the document U.S. Pat. No. 5,463,467 in which an activation of light-emitting diodes is described for carrying out photometric analyses. The present invention also envisages activating light sources by means of signals which enable the influence of foreign light to be eliminated from the detected signal as described for example in the said document U.S. Pat. No. 5,463,467.

An important step in the method according to the invention is to compare the detected signals and determine which of the signals or whether both signals have been obtained by illumination of an area which lies completely on the detection zone. This determination can be carried out in various ways. If the analyte results in a colour forming reaction in the detection zone, the first and second detection signal can be compared and the light signal that has been more greatly attenuated is selected as lying completely on the detection zone. If in contrast a reaction is carried out in which colour is degraded by the analyte, the signal which has been subjected to the least attenuation is selected as the one which is located completely on the detection zone. These two procedures can be carried out without having to carry out a measurement on the detection zone before reaction with the analyte in order to determine a blank value. However, according to the invention it is preferred that first measurements are carried out on the detection zone with a first and second light source before carrying out the reaction with the sample. The detection signals determined in this manner can be used as a basis for determining which signal results from an irradiated area that is located completely within the detection zone and as a base value (so-called blank value) for determining the analyte concentration. If measurements have been carried out with the light sources on a test element that has not yet reacted, then the inventive determination step can be advantageously carried out by determining the signal amplitude before and after reaction of the detection zone with the sample and selecting that light source for the determination of the analyte concentration which yielded the larger signal amplitude.

The selection of at least one of the two light sources as suitable for determining the analyte concentration can also be carried out without having to contact the detection zone with the sample. This can for example be achieved when the detection zone is composed of a light material and the test element has a dark colour in the area bordering the detection zone. If measurements are carried out on such a test element with a first and second light source and the measurements are compared, the light source from which the higher reflectance signal was obtained can be selected as being suitable for determining the analyte concentration. It is additionally possible to make the detection zone at least partially transparent whereas the area of the test element bordering the detection zone is essentially impermeable to light. If a transmission measurement is now carried out, the light source can be selected with which a higher transmission was obtained. If reference was made above to a higher or lower signal, this can mean a "crude signal" which is present at the detector when the light sources are activated. The crude signals are advantageously corrected before comparing them i.e. the illumination geometry and the variation of intensity from light source to light source are taken into account. This can for example be achieved by standardizing the signals on the basis of blank values (forming a ratio between the actual signal and the signal for an unreacted test element or standard).

The present invention additionally concerns a method for the photometric analysis of a test element in which sample application is detected. In this method as so-called control area of the detection zone of a test element is firstly irradiated and the radiation reflected from this control area or transmitted through the control area is monitored. In this connection monitoring means that the reflected or transmitted radiation is measured at intervals. Usually measurements are carried out at intervals of fractions of a second. The time intervals are selected in practice such that the time interval between two measurements is less than the time delay which can be tolerated for the detection of a change in the measured value. During the monitoring of the control area, a sample liquid is supplied to the detection zone and this is carried out in such a manner that a first zone of the detection zone comes into contact with the sample liquid earlier than a second zone which is laterally spaced from the first zone. In this connection the term lateral refers to the plane of the detection zone. Hence there is a spacing between the first and the second zone when the detection zone is observed from the upper side. Such a transport of sample liquid to a detection zone occurs for example in chromatographic test strips in which the sample or a reaction solution of the sample penetrates from one side into the detection zone and laterally migrates through the detection zone. Such a supply of sample liquid also occurs when a capillary gap test element is used in which the capillary gap and detection zone are disposed in the same plane. This can for example be achieved in such a manner that the capillary gap ends at an edge of the detection zone and sample liquid from the capillary gap penetrates from this site of contact into the detection zone or the capillary gap can be located below the detection zone as shown in FIG. 1. In the said cases the sample liquid comes into contact with the first zone of the detection zone earlier than with a second zone. In FIG. 6 this is indicated by the zones Z1 and Z2. The sample liquid penetrates via a capillary gap which is located below the detection zone (10) into the detection zone in the direction of the arrow. In this case the zone Z1 comes into contact with the sample liquid earlier than zone Z2.

In the method according to the invention a sample application is detected on the basis of a change in the reflected or transmitted radiation in the control area. In this connection a change means that a signal change occurs during the monitoring i.e. the transmission or reflection signals obtained from the unreacted control area of the detection zone are different from those obtained from a control area which is moistened thoroughly with sample liquid or which has reacted with sample liquid.

In order to analyse the test element, at least one detection area of the detection zone is irradiated and the radiation that is reflected from this area or transmitted through the detection area is detected and analysed in order to determine the concentration of an analyte in the sample liquid. Details on the detection and analysis have already been described above for an inventive method for compensating positioning tolerances.

Monitoring the control area enables an earlier detection of the presence of sample liquid in the control area than when measuring in the detection area. When liquid is detected a signal can be emitted which terminates supply of sample liquid. The signal can be an optical and/or an acoustic signal. In the case of a capillary gap test element this for example means that blood supply to the capillary gap can be terminated. Consequently it is possible to prevent unnecessary supply of further sample liquid and thus to reduce the required amount of sample and on the other hand this procedure shortens the time required to supply sample liquid which is convenient for the user. Nevertheless the method according to the invention still ensures that the detection area or detection areas of the detection zone are adequately supplied with sample liquid. For this purpose it is advantageous when the detection area is nearer than the control area to the first zone which firstly comes into contact with the sample liquid. Thus the test element is wetted with sample liquid in the area of the detection zone earlier than in the area of the control zone and when sample liquid is present in the area of the control zone it is ensured that the detection zone is also supplied with sample liquid. According to the invention it is also preferred that the control area (area A in FIG. 6) is irradiated with radiation that is absorbed by the sample liquid itself. Even if the sample liquid does not itself absorb radiation or only partially absorbs radiation there is usually a decrease in the reflected or transmitted radiation when the control zone is moistened. As a result the presence of sample liquid can already be determined before a reaction with reagents has taken place in the detection zone. FIG. 7 shows that a decrease in reflection in area A of the detection zone shown in FIG. 6 is already found in the time interval II. This is due to the fact that a thorough moistening of the control area A can be very rapidly detected by a 880 nm light-emitting diode. Detection of a wetting of this area on the basis of a colour formed in the detection zone would not have been possible until time interval IV. In the method according to the invention in which sample application is detected, the control area is preferably on the detection zone. This not only reduces the time until detection but also allows a compact construction of such an instrument in which the optical components can be in close vicinity to one another.

BRIEF DESCRIPTION OF THE DRAWINGS

The present invention is elucidated in more detail in the following on the basis of some figures:

FIG. 1: Perspective and cross-sectional representation of a capillary gap test element FIG. 5: Position of irradiated areas on the detection zone

DESCRIPTION OF PREFERRED EMBODIMENTS

Figure 2:
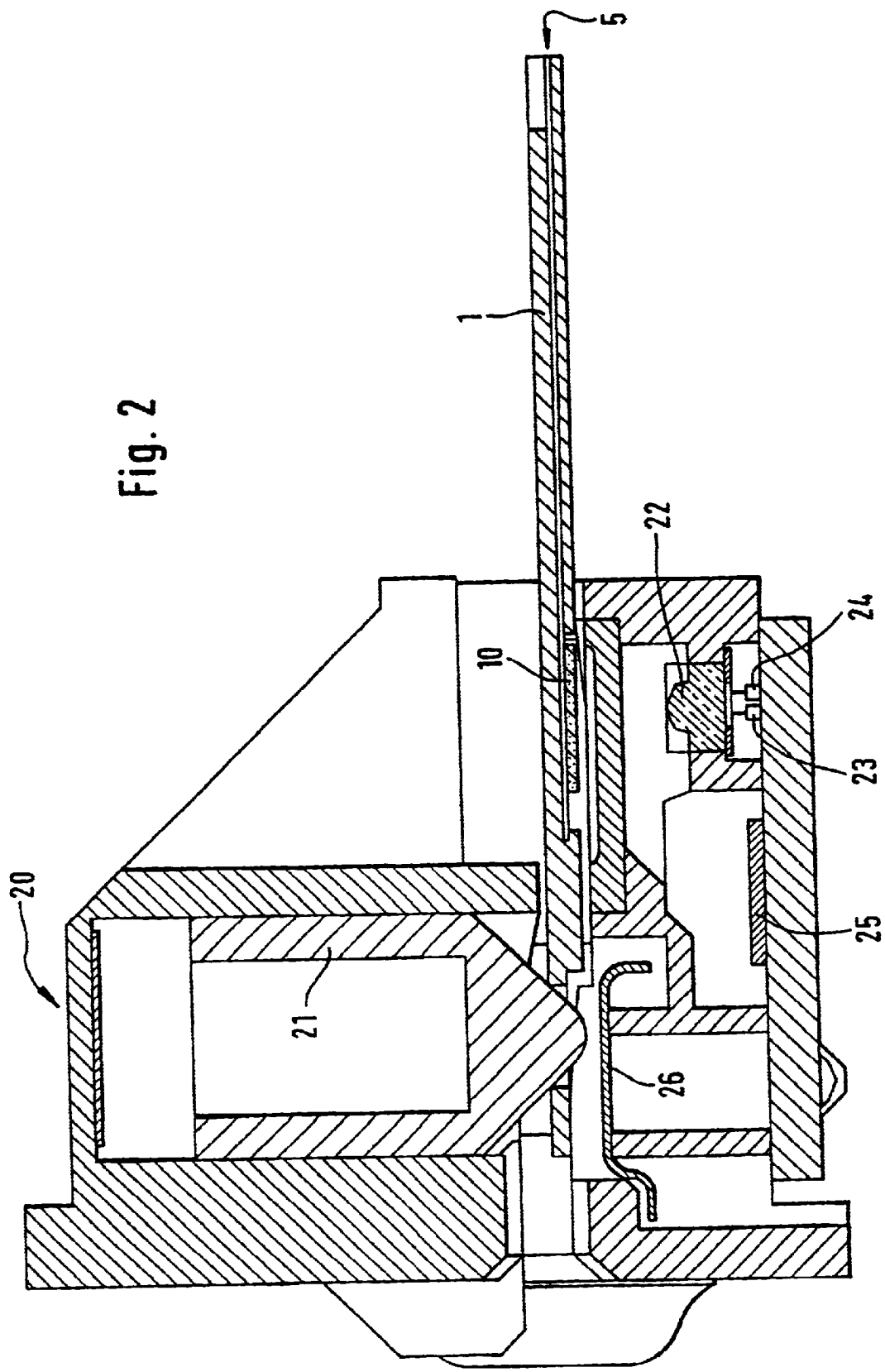
FIG. 2: Cross-section through a device lengthwise to an inserted test element

FIG. 1A shows a perspective view of a capillary gap test element. The test element has a carrier foil (2) and a cover foil (3). A spacer (4) which has a recess is located between these foils to form a capillary gap between the carrier foil and cover foil. In order to carry out a diagnostic test, sample liquid which is usually capillary blood is brought to the opening (5) of the capillary gap. The sample liquid is moved through the channel due to capillary forces and reaches the reagent paper (6). The reagent paper (6) is in turn also mounted on a spacer (4) so that only the middle part of the reagent paper is wetted with sample when sample liquid is present in the capillary gap (7) and only this part forms a colour or generates a signal. This middle region that can be used to determine the analyte concentration is referred to as the detection zone (10). In the example shown the detection zone has a size of ca. 2×3 mm. Such a small detection zone gives rise to two particular problems concerning the measurement. On the one hand the signal obtained from the detection zone must be of adequate strength to allow a reliable determination of the analyte concentration and, on the other hand, it must be ensured that when analysing the detection zone there are no contributions from reflectance from outside the detection zone. In practice both requirements are closely linked since in order to increase the measurement signal one will try to measure the detection zone as completely as possible which, however, means that there is a risk of obtaining contributions from outside the detection zone if one cannot guarantee an exact positioning of the detection zone relative to the illumination unit. The problem of positioning is particularly pronounced in capillary gap test elements since there is a relatively large variation in the position of the capillary gap as a result of the manufacturing process. However, the present invention enables in a simple manner, on the one hand, analysis of a relatively large part of the detection zone and, on the other hand, avoidance of erroneous contributions from regions outside the detection zone.

FIG. 2 shows a cross-sectional view of a device according to the invention (20) lengthwise to a test element (1). The device (20) has a channel in which a test element (1) can be inserted. FIG. 2 shows the positioning of a test element in an analytical position. The device has a movably mounted pin (21) with a downwards tapering conical end to hold the test element in this position when the positioning is suitable, the tip of the pin is located in a recess of the test element such that the test element is fixed and positioned in the direction of its longitudinal axis. The pin (21) can also be used to electrically signal the presence of a test element or its positioning. For this purpose the pin is designed to be electrically conductive and a contact (26) is provided on the opposing side of the device. When a test element is not present, the pin is pressed against the contact (26) by a spring which makes an electrical contact between these two elements. If a test element is now inserted, it slides firstly between the pin (21) and contact (26) and thus breaks the electrical contact. However, when it is slided further, the pin (21) engages through the groove of the test element and the electrical contact closes again.

FIG. 2 shows another optical arrangement for analysing the test element. In the analytical position the detection zone (10) of the test element is positioned relative to a lens (22) on the opposite side of which light sources (23, 24) are located. The light source (23) is used to illuminate the detection zone in order to determine an analyte concentration. Light source (24) illuminates a zone on the detection zone which is at a greater distance from the application opening (5) for the sample liquid than the zone illuminated by the light source (23). Hence the light source (24) can be used to carry out the method according to the invention for detecting sample application. Due to the required degree of miniaturization the light sources (23, 24) are in the form of light-emitting diodes which are directly mounted on the semiconductor circuit board.

FIG. 2 also shows a semiconductor detector (25) which detects radiation reflected from the detection zone.

Figure 3:
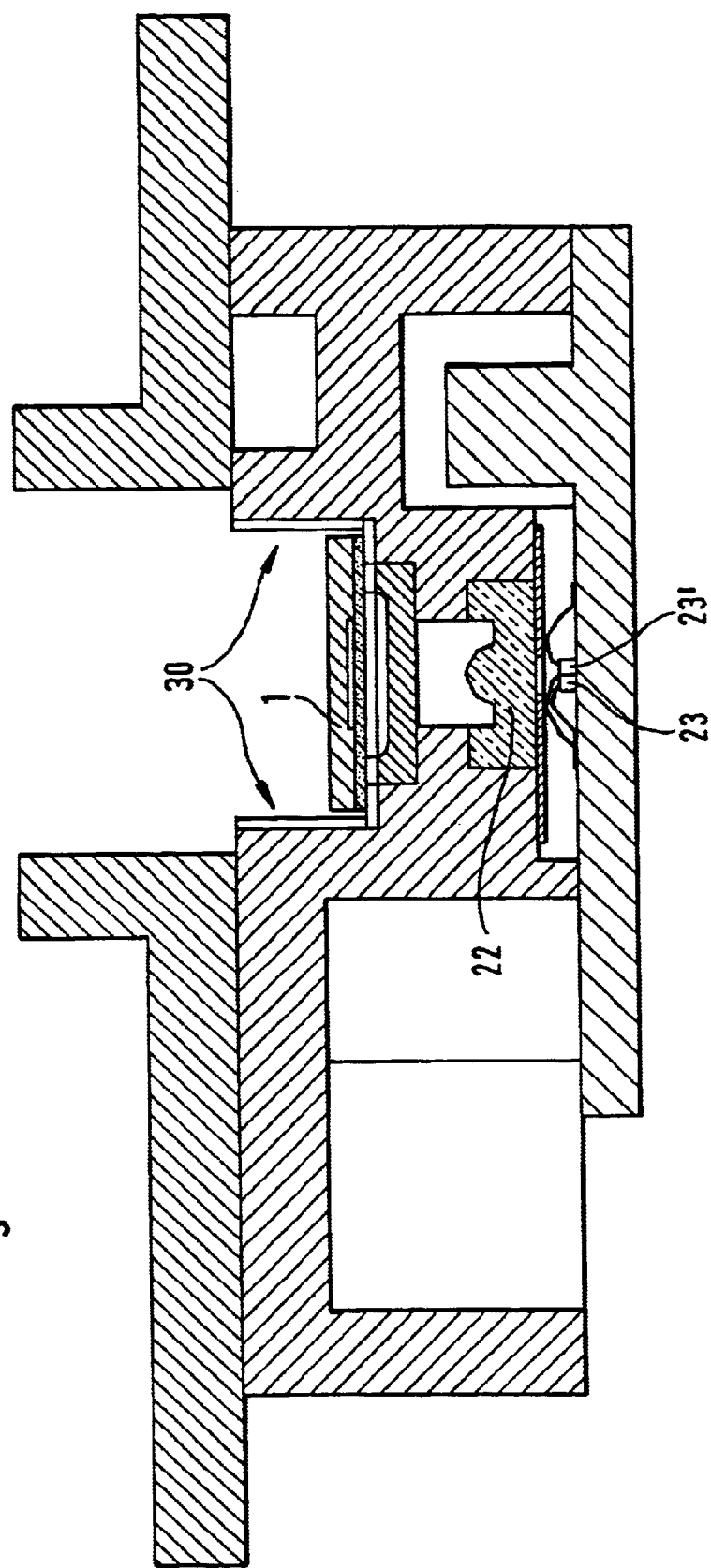
FIG. 3: Cross-section through a device at right angles to the test element

The lateral positioning of the test element in the device is shown in FIG. 3. The test element (1) is located in a channel (30) which prevents lateral movement as far as possible. As a result of the manufacturing tolerances of the test elements, the dimensions of the channel (30) must be such that it can also receive the largest expected test elements. This means that due to manufacture, it is not possible to ideally position smaller test elements in the channel (30) and lateral movement is possible. The method according to the invention can be used to nevertheless reliably measure a signal of the detection zone for all test elements which originates from an illuminated region which is completely on the detection zone. For this purpose the device has the light sources (23, 23') which are arranged next to one another in a direction perpendicular to the test element. It is advantageous for the optical arrangement when the light sources are focused on the detection zone of the test element by means of a lens (22) or a lens system. The distance between the light sources and between the light sources and detection zone and the design of the lens (22) is selected such that the boundary conditions elucidated below in connection with FIG. 5 are met.

Figure 4:
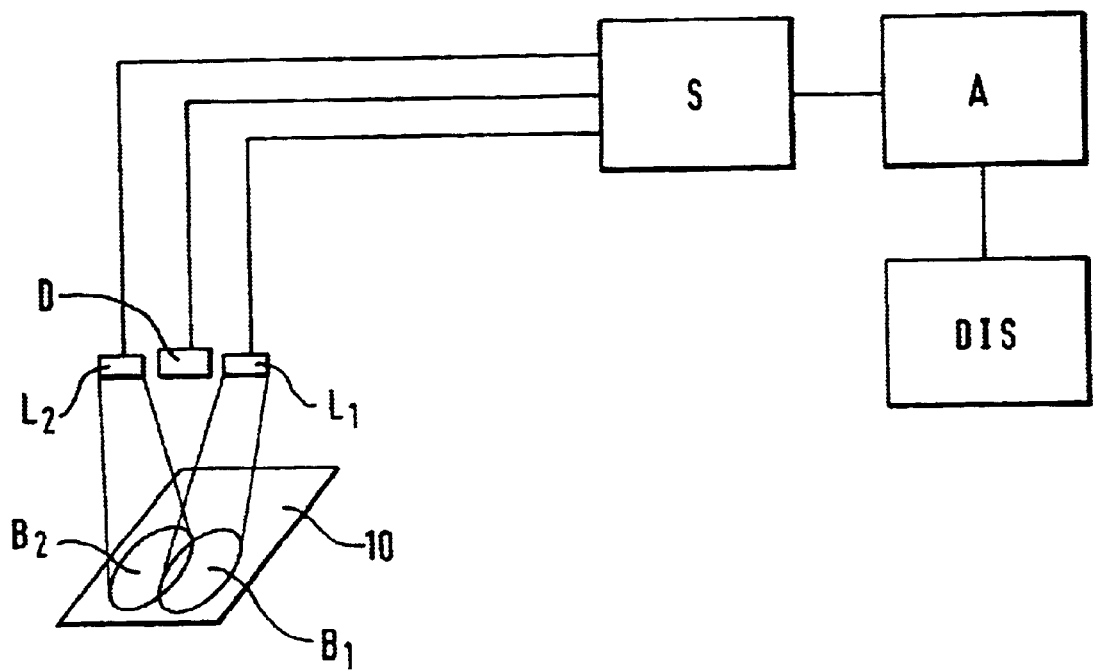
FIG. 4: Block diagram of an analytical device

FIG. 4 shows a schematic block diagram of a device for the photometric analysis of test elements. The first light source L1 and the second light source L2 are arranged next to one another such that they illuminate different but overlapping regions B1 and B2 on the detection zone (10). The detector (D) receives the diffusely reflected radiation from the detection zone (10) and passes the corresponding signal to the control unit (S). The control unit successively activates the light sources L1 and L2 and registers each of the signals received by the detector. These signals are passed onto the evaluation unit (A) where the signals are compared and a suitable signal is selected as described above. In the example shown both regions B1 and B2 are completely on the detection zone (10) and thus both can be used to calculate the analyte concentration. Hence one of the signals is used to calculate an analyte concentration in a known manner which is then passed onto the display (DIS). In the present case an averaged signal can also be used to determine the concentration.

FIG. 5 shows some examples of how the irradiated regions can be arranged relative to one another and relative to the detection zone. FIG. 5A shows a particularly preferred embodiment in which the illuminated regions B1 and B2 have an oval shape and partially overlap. In the example shown the signal detected from the illuminated region B2 is used to calculate the analyte concentration since this region is located completely on the detection zone (10) whereas a signal obtained from the region b1 is falsified due to contributions from outside the detection zone. FIG. 5A additionally shows a coordinate system which is intended to simplify the description of the figures. The arrangement of illuminated regions selected in FIG. 5A is intended to compensate a positioning tolerance of the detection zone in the direction of the X axis. In this case the illuminated regions are selected such that a connecting line through their focal points is essentially parallel to the direction in which a positioning tolerance is expected or to be compensated. FIG. 5B shows an embodiment which enables the positioning tolerance to be compensated in the direction of the X axis as well as of the Y axis. In this case four illuminated regions have been selected which are displaced relative to one another in the direction of the X and the Y axis. Since the regions B1, B3 and B4 result in reflectances with components from outside the analytical zone, the region B2 is used for the analysis since this is completely within the detection zone.

FIG. 5C shows an embodiment which can compensate for particularly large variations in the position of the detection zone in the direction of the X axis. Three illumination regions that are spaced apart have been selected in the direction of the X axis in which the positioning tolerance is critical. If only regions B1 and B2 would have been used, a suitable analysis would not have been possible, but this is now possible by means of region B3.

FIG. 5D shows a less preferred embodiment in which the illuminated regions B1 and B2 do not overlap and there is even a clear region between them. As shown in the figure positions can occur with this arrangement in which an exact analysis is not possible with either of the illuminated regions. Hence within the scope of the present invention it is preferred that the illuminated regions overlap or at least are directly adjacent to one another.

FIG. 5E also shows a less preferred embodiment. In this case the illuminated regions are selected to be so large that both extend beyond the detection zone when the detection zone is positioned centrally. The detection zone cannot be exactly analysed with either of the two regions. Hence within the scope of the present invention it is preferred that the total width (b) of the two light sources is smaller than the corresponding width of the detection zone. Hence the size of each individual illuminated region must be smaller than that of the detection zone. As already mentioned the aim should be to make the illuminated regions as large as possible in order to obtain a maximum signal yield and thus a good signal/noise ratio. In the individual case a compromise must be reached between the size of the illuminated regions and their overlap which on the one hand ensures that always one of the illuminated regions is completely on the detection zone with the expected positioning tolerances and, on the other hand, that the signal obtained from an individual illuminated region is large enough to ensure the required accuracy of the analysis.

FIG. 5F shows a diagram that can be used to determine the maximum allowable positioning tolerance for a given arrangement. Two illuminated regions B1 and B2 are shown which each have a width (d) in the direction of the positioning tolerance. The illuminated regions B1 and B2 overlap in the direction of the positioning tolerance by the distance "a" so that the overall width "b" is 2d−a. In the limiting position P1 is still completely on the detection zone whereas the opposite limiting position P2 (dashed) the region B1 is still just completely on the detection zone. Hence the maximum variation in positioning that can be tolerated by the arrangement is X−a in which X is the width of the detection zone in the direction of the positioning tolerance. If the width X of the detection zone is known and also the maximum shift of position that can occur from one extreme position into the other ($T_{max}$) then it is possible to calculate the required overlap "a" of the illuminated regions as X−$T_{max}$.

As already mentioned the width b; (b=2d−a) should be smaller than X in order to avoid the case shown in FIG. 5E. If this is generalized for different diameters (d1, d2) it follows that d1+d2−a<X. If the required overlap has been accordingly selected with regard to the expected positioning tolerance, then this allows the maximum diameter d (or the width in the case of regions that are not round) of an individual illuminated region to be calculated as follows: d=(X+a)/2. The maximum overlap of the regions should be preferably selected such that it is smaller than half the diameter of the width (a<(d1+d2)/2). As a rule it is not only the linear overlap "a" that is important for a suitable selection of the overlap, but also the ratio of the size of the overlapping area ($F_{\ddot{u}}$) to the area of an irradiated region ($F_B$). It turned out experimentally that $F_{\ddot{u}}/F_B$ is advantageously less than 0.3 and particularly advantageously between 0.2 and 0.1.

The above-mentioned geometric considerations should not obscure the fact that experiments are usually necessary to determine the optimal relationships. This is partly due to the fact that the illuminated regions shown only partly describe the true conditions. Usually it can be assumed that it is reasonable to make the calculations on the basis of regions that represent about 90% of the total intensity. However, this means that a certain proportion of reflected radiation already comes from outside the detection zone if the marked illuminated region is at the border. Furthermore a problem in practice is that there are manufacturing variations in the adjustment of the light sources and thus tolerances in the overlap of the illuminated regions also have to be taken into account. Hence in practice one would preferably design a device according to the invention such that in an extreme position at least one of the light sources completely irradiates the detection zone and is at a distance of ca. 10% of the light spot diameter from the nearest edge of the detection zone.

Figure 6:
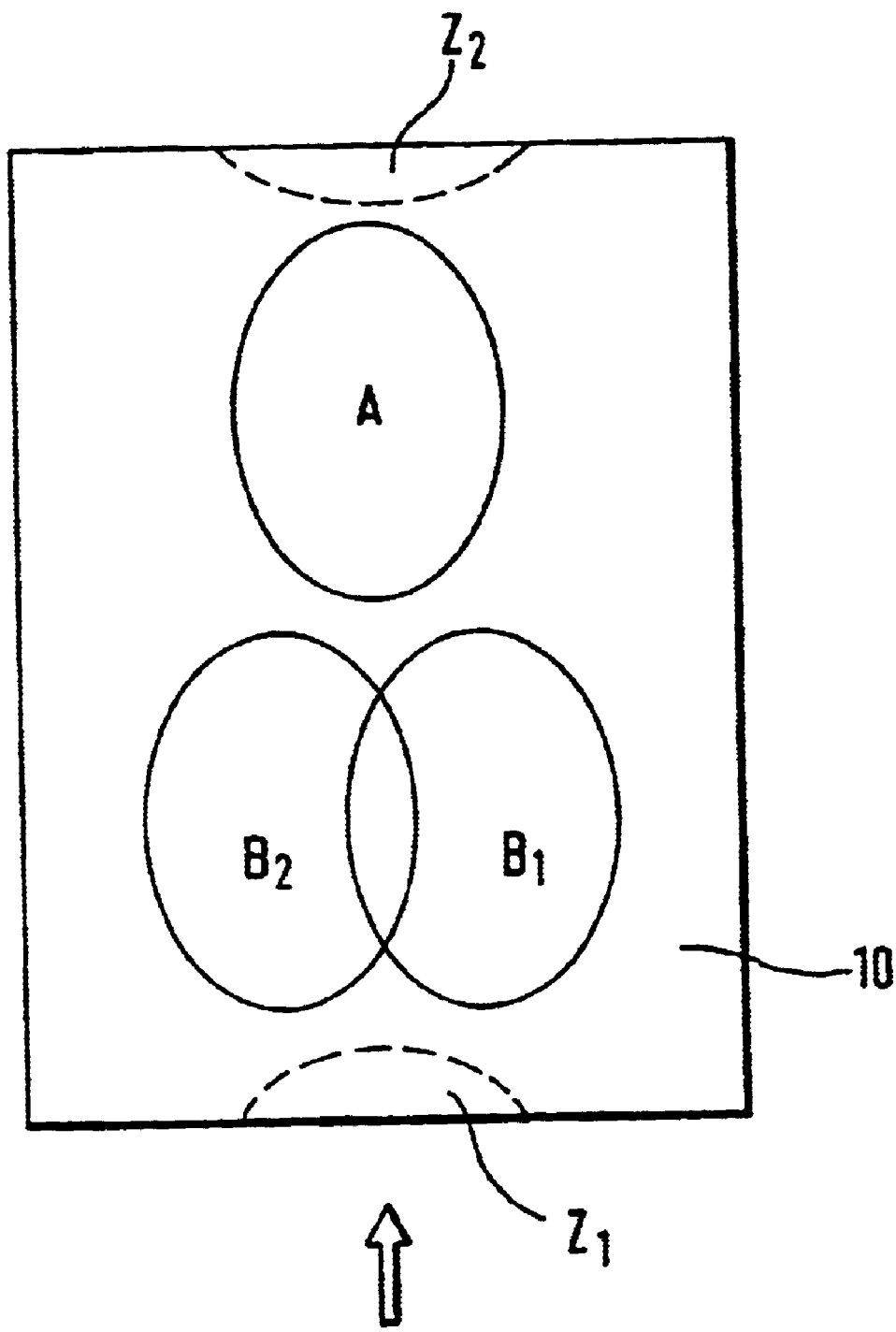
FIG. 6: Irradiated areas on the detection zone

FIG. 6 shows a detection zone and the irradiated regions B1, B2 and region A. The arrow in FIG. 6 shows the direction of flow of sample liquid in a capillary gap test element according to FIG. 1. Accordingly the liquid firstly comes into contact with the detection zone below the regions B1 and B2 and subsequently with zone A. The position of region A is advantageously selected such that it is not overlapped or only partly overlapped by the regions B1 and B2. Whereas regions B1 and B2 are preferably analysed in a wavelength range which is absorbed by the colour formed in the detection zone but not by the sample as such, a wavelength is preferably used to measure region A in which the sample itself absorbs. In the case of aqueous liquids infrared radiation which is in the range of the water bands can for example be used to analyse region A. However, it is preferable to use a wavelength in the range of 800 to 950 nm which can be used to detect an absorption of the intrinsic colour of blood. After applying sample liquid to a capillary gap test element according to FIG. 1, region A is continuously measured and the radiation transmitted through the detection zone or reflected from the detection zone is detected. This can be achieved with the same detector that is also used for the subsequent analysis of regions B1 and B2. However, it is preferable to use a special detector that is adapted to the irradiation range used for region A.

Figure 7:
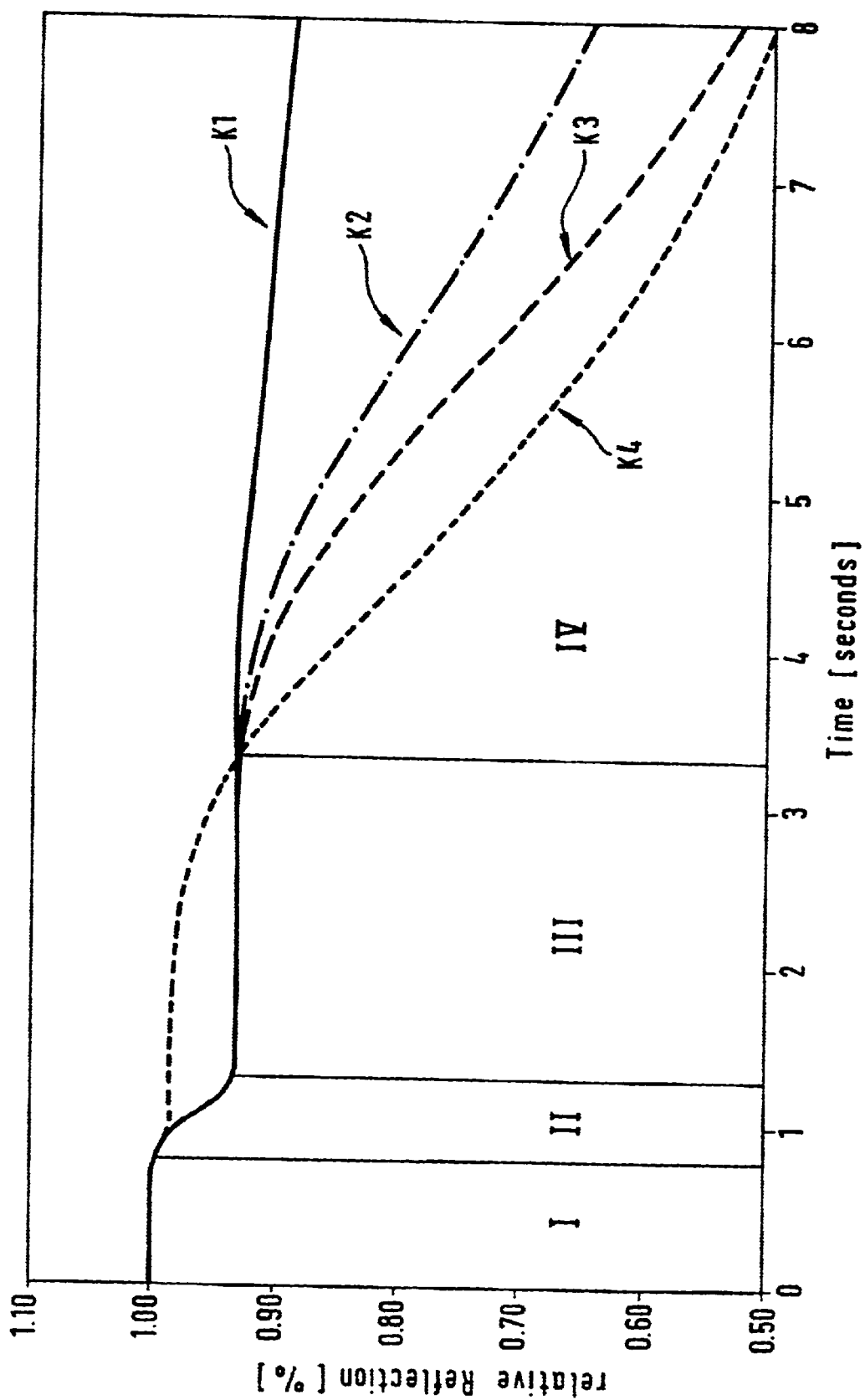
FIG. 7: Signal time course measured in the control area

FIG. 7 shows the signal time course obtained from the analysis of region A. At time 0 blood fluid is applied to the capillary gap. During the time interval I no significant reduction in reflectance is measured in region A for all curves. A reduction in reflectance is found in range II for the curves K1, K2 and K3 (glucose concentration: K1:25 mg/dl; K2:250 mg/dl; K3:500 mg/dl) which were recorded with capillary blood. The decrease in reflectance shows that the sample liquid has arrived. The instrument can now indicate to the user that he can stop adding the sample liquid since sufficient liquid is present to carry out the analytical test. The advantage for the user is that he can use smaller amounts of blood and the time required for the application can be shortened. A continuous decrease in reflectance is seen in range IV in FIG. 7 which is due to the formation of colour in the detection zone. This shows that an indication of sufficient sample being present based on colour formation in the detection zone would not have been possible until seconds later since the colour formation requires a certain time. The gain in time of 3 to 4 seconds already represents a considerable gain in comfort for the user.

FIG. 7 in addition shows the curve K4 which was obtained from a colourless glucose solution and detection at 880 nm. In contrast to the curves K1, K2 and K3, this curve shows no significant decrease in reflectance in the time ranges II and III, but only in range IV when colour formation begins. Hence on the basis of the time course of the signal detected in region A of the detection zone it is possible to differentiate between sample liquid, in particular blood, and a glucose solution used as a control or to calibrate the instrument. If the instrument recognizes that a control solution has been used then it can carry out a measurement and calibrate itself. In this case a correction factor can for example be used which is calculated from the ratio between the measured concentration and the true concentration of the control solution. Subsequent measured values can then be automatically corrected by the instrument by dividing by the correction factor. The true concentration of the control solution can for example be stored in the instrument especially when only one set control solution is used or the concentration can be entered into the instrument by the user.

Figure 8:
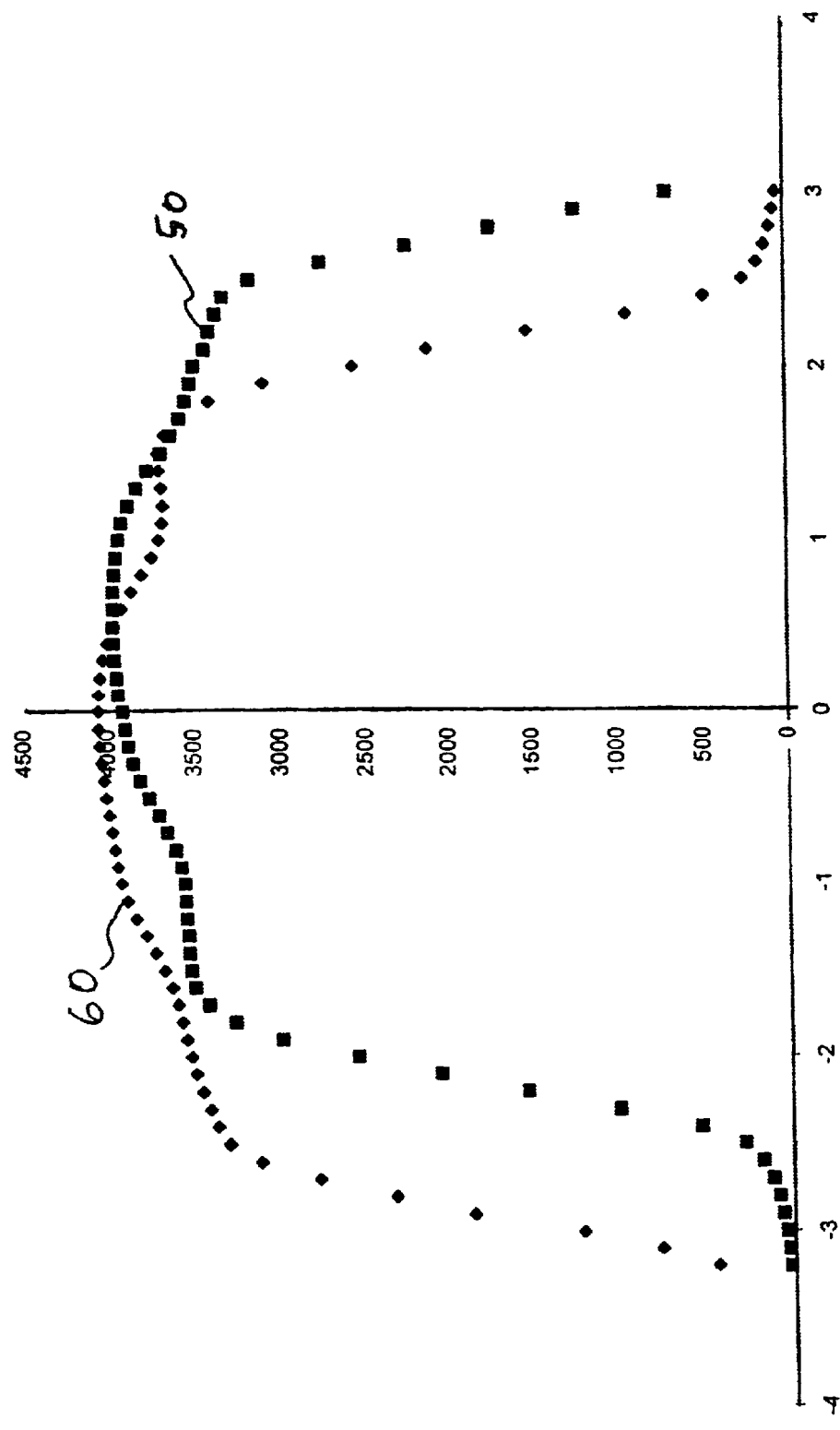
FIG. 8: Signal time course when the test element is displaced.

FIG. 8 shows two signal curves measured at the detector (25; FIG. 2) for different positions of the test element. The relative position of the test element in millimeters is shown on the abscissa of the figure.

The position of the test element (1) shown in FIG. 3 in which the capillary gap (5) is located centrally above the lens (22) represents the zero position. Positive values of the abscissa represent a lateral displacement of the test element at right angles to the capillary gap. Hence FIG. 8 shows how the measured signal behaves when the test element is not positioned centrally or/and the capillary gap is not arranged centrally on the test element as a result of the manufacturing.

The signals measured at the detector are shown in arbitrary units on the ordinate. Diffusely reflected radiation is detected by the test element as a result of the selected measuring geometry shown in FIGS. 2 and 3.

The signal curves shown in FIG. 8 show that the signals are highest near to the zero position. This is due to the fact that the measurements were carried out on a white reagent paper (6) without sample application. The reflectance is highest before sample application in the region of the reagent paper below which the capillary gap is located and which is used as the actual measurement region after sample application.

The reflectances are somewhat lower outside this region although reflectance is still obtained from the reagent paper. This is due to the fact that a coloured foil has been glued to the back of the reagent paper in these regions.

Curve 50 which is composed of measurement points that are shown as squares, shows the signal curve when the light source (23) is activated. In contrast curve 60 which is composed of measurement points that are shown as rhombi shows the signal curve when the test element is displaced when the light source (23') is activated.

FIG. 8 shows that in the range of ca. 0 to +1 mm it is possible to carry out a measurement with light source (23) and a measurement with light source (23') in the range of ca. −1 to 0 mm. Hence the arrangement can tolerate a positioning tolerance of ±1 mm.

What is claimed is:

1. A method for the photometric analysis of test elements having a detection zone, the method being tolerant of positioning variations of the detection zone, comprising the steps of
 a) placing a test element in a holder such that the detection zone of the test element is positioned relative to an illumination unit having a first and a second light source, a positioning variation of the detection zone occurring in at least one direction,
 b) contacting the detection zone with a sample such that a detection system present in the detection zone leads to a photometrically detectable change in the detection zone when an analyte is present in the sample, c) activating the first light source to irradiate a first region of the detection zone, and detecting at least one of light reflected from the detection zone or light transmitted through the detection zone, in order to generate a first detection signal, d) activating the second light source to irradiate a second region of the detection zone which is displaced relative to the first region in the direction of the positioning variation and detecting at least one of light reflected from the detection zone or light transmitted through the detection zone in order to generate a second detection signal, e) comparing the first and the second detection signal and determining whether the first and/or the second detection signal has been obtained by illuminating an area situated completely on the detection zone and selecting the corresponding detection signal; and f) determining the analyte concentration contained in the sample by analysing the selected signal.

2. A method as claimed in claim 1, further comprising the steps of:

a) determining a first and a second base-line detection signal on an unused test element, and b) standardizing the first and the second detection signal by division by the corresponding base-line detection signal before determining the analyte concentration in step f).

3. A method as claimed in claim 1, wherein the first region irradiated by the first light source and the second region irradiated by the second light source have essentially the same size.

4. A method as claimed in claim 1, wherein the test element is a capillary gap test element.

5. A method as claimed in claim 1, further comprising the step of: arranging the first and second light source such that focal points of the light sources are located in a connecting line running essentially parallel to a width of the detection zone.

6. A method as claimed in claim 5, wherein the test element is a capillary gap test element containing a capillary gap, and the width is arranged essentially perpendicular to the capillary gap.

7. A method as claimed in claim 5, wherein the first region has a width d1 and the second region has a width d2, and the first and second regions overlap over a maximum width "a" in the direction of the connecting line whereby the following applies:

$$d1+d2-a<X,$$

where X is the width of said detection zone.

8. A method as claimed in claim 7, in which the following applies:

$$a<(d1+d2)/2.$$

9. A method as claimed in claim 1, wherein the regions irradiated by the first light source and by the second light source are ovals.

10. A method as claimed in claim 1, wherein the regions irradiated by the first light source and by the second light source are rectangles.

11. A method as claimed in claims 1, 9 or 10, wherein the first and second irradiated regions overlap.

12. A method as claimed in claim 11, wherein the maximum overlap is less than half the diameter of the irradiated regions.

13. A method for the photometric analysis of test elements having a detection zone, the method being tolerant of positioning variations of the detection zone, comprising the steps of a) placing a test element in a holder such that the detection zone of the test element is positioned relative to an illumination unit having a first and a second light source, a positioning variation of the detection zone occurring in at least one direction, b) contacting the detection zone with a sample such that a detection system present in the detection zone leads to a photometrically detectable change in the detection zone when an analyte is present in the sample, c) activating the first light source to irradiate a first region of the detection zone, and detecting at least one of light reflected from the detection zone or light transmitted through the detection zone, in order to generate a first detection signal, d) activating the second light source to irradiate a second region of the detection zone which is displaced relative to the first region in the direction of the positioning variation and detecting at least one of light reflected from the detection zone or light transmitted through the detection zone in order to generate a second detection signal, e) comparing the first and the second detection signal and determining whether the first and/or the second detection signal has been obtained by illuminating an area situated completely on the detection zone and selecting the detection signal that has a lower intensity, and f) determining the analyte concentration contained in the sample by analysing the selected detection signal.

14. A method for the photometric analysis of test elements having a detection zone, the method being tolerant of positioning variations of the detection zone, comprising the steps of a) placing a test element in a holder such that the detection zone of the test element is positioned relative to an illumination unit having a first and a second light source, a positioning variation of the detection zone occurring in at least one direction, b) contacting the detection zone with a sample such that a detection system present in the detection zone leads to a photometrically detectable change in the detection zone when an analyte is present in the sample, c) activating the first light source to irradiate a first region of the detection zone, and detecting at least one of light reflected from the detection zone or light transmitted through the detection zone, in order to generate a first detection signal, d) activating the second light source to irradiate a second region of the detection zone which is displaced relative to the first region in the direction of the positioning variation and detecting at least one of light reflected from the detection zone or light transmitted through the detection zone in order to generate a second detection signal, e) activating at least one further light source which irradiates a third region and detecting a change in at least one of reflected or transmitted light from the third region to detect the presence of the sample f) comparing the first and the second detection signal and determining whether the first and/or the second detection signal has been obtained by illuminating an area situated completely on the detection zone and selecting the corresponding detection signal, and g) determining the analyte concentration contained in the sample by analysing the selected detection signal.

15. A method as claimed in claim 14, wherein the at least one further light source emits radiation in a second wavelength range that is different from that of the first and second light sources and radiation in this second wavelength is detected in order to detect the presence of sample.

16. A method as claimed in claim 15, wherein the second wavelength range is in the range of 800 to 950 nm.

17. A method as claimed in claim 14, wherein the third region is located on the detection zone.

18. A method as claimed in claim 17, wherein the sample is brought into flow contact with the detection zone and the third region is located downstream of the first and second region.

19. A device for the photometric analysis of test elements comprising:

an illumination unit comprising at least a first and a second light source, a holder for holding a test element with a detection zone in such a manner that the detection zone is positioned relative to the illumination unit, a control unit which activates the first light source during a first activation phase in order to illuminate a first region of the detection zone and activates the second light source during a second activation phase in order to illuminate a second region of the detection zone, a detection unit with at least one detector which detects light reflected from the detection zone or transmitted through the detection zone, the signal generated by the detection unit during the first activation phase being recorded as the first detection signal and the signal generated during the second activation phase being recorded as the second detection signal, an analytical unit which compares the first and second detection signal and determines whether the first and/or the second detection signal has been obtained by illuminating a region situated completely on the detection zone, and analyses a corresponding analyte detection signal in order to determine an analyte concentration in a sample.

20. A device for the photometric analysis of test elements comprising:

an illumination unit comprising at least a first and a second light source, and at least one additional third light source which emits radiation in a second wavelength range that is different from that of the first and second light sources, a holder for holding a test element with a detection zone in such a manner that the detection zone is positioned relative to the illumination unit, a control unit which activates the first light source during a first activation phase in order to illuminate a first region of the detection zone and activates the second light source during a second activation phase in order to illuminate a second region of the detection zone, a detection unit with at least one detector which detects light reflected from the detection zone or transmitted through the detection zone, the signal generated by the detection unit during the first activation phase being recorded as the first detection signal and the signal generated during the second activation phase being recorded as the second detection signal, an analytical unit which compares the first and second detection signal and determines whether the first and/or the second detection signal has been obtained by illuminating a region situated completely on the detection zone, and analyses the radiation transmitted or reflected in said second wavelength range in order to determine an analyte concentration in a sample.

21. A device as claimed in claim 20, wherein the second wavelength range is 800 to 950 nm.

22. A device as claimed in claim 20, wherein the third light source irradiates a region of the detection zone which does not overlap with the first and second regions.

23. A method for the photometric analysis of a test element with detection of sample application on a flat detection zone of the test element comprising the steps irradiating a control region of the detection zone, supplying sample liquid to the detection zone in such a manner that a first zone of the detection zone comes into contact with sample liquid earlier than a second zone which is laterally displaced from the first zone, monitoring radiation reflected from the control region or transmitted through the control region, detecting presence of the sample liquid in the control region from a change of the reflected or transmitted radiation, irradiating at least one detection region of the detection zone, wherein the detection region is nearer to the first zone than the control region, detecting radiation reflected from or transmitted through the detection region, generating a signal that can be recognized by a user of the test element to terminate supply of sample liquid when the presence of sample liquid is detected in the control region, and analysing the detected radiation to determine the concentration of an analyte in the sample liquid.

24. A method as claimed in claim 23, wherein the test element includes a capillary gap.

25. A method as claimed in claim 24, wherein the capillary gap runs below the detection zone.

26. A method as claimed in claim 23, wherein the detection region is nearer to the first zone than the control region.

27. A method as claimed in claim 23, wherein the control region is irradiated with radiation that is absorbed by the sample liquid.

28. A method as claimed in claims 23 or 27, wherein the detection region is irradiated with radiation that is essentially not absorbed by sample liquid.

29. A method as claimed in claim 23, wherein the signal that can be recognized by a user is an optical and/or an acoustic signal.

* * * * *